Figure 1:
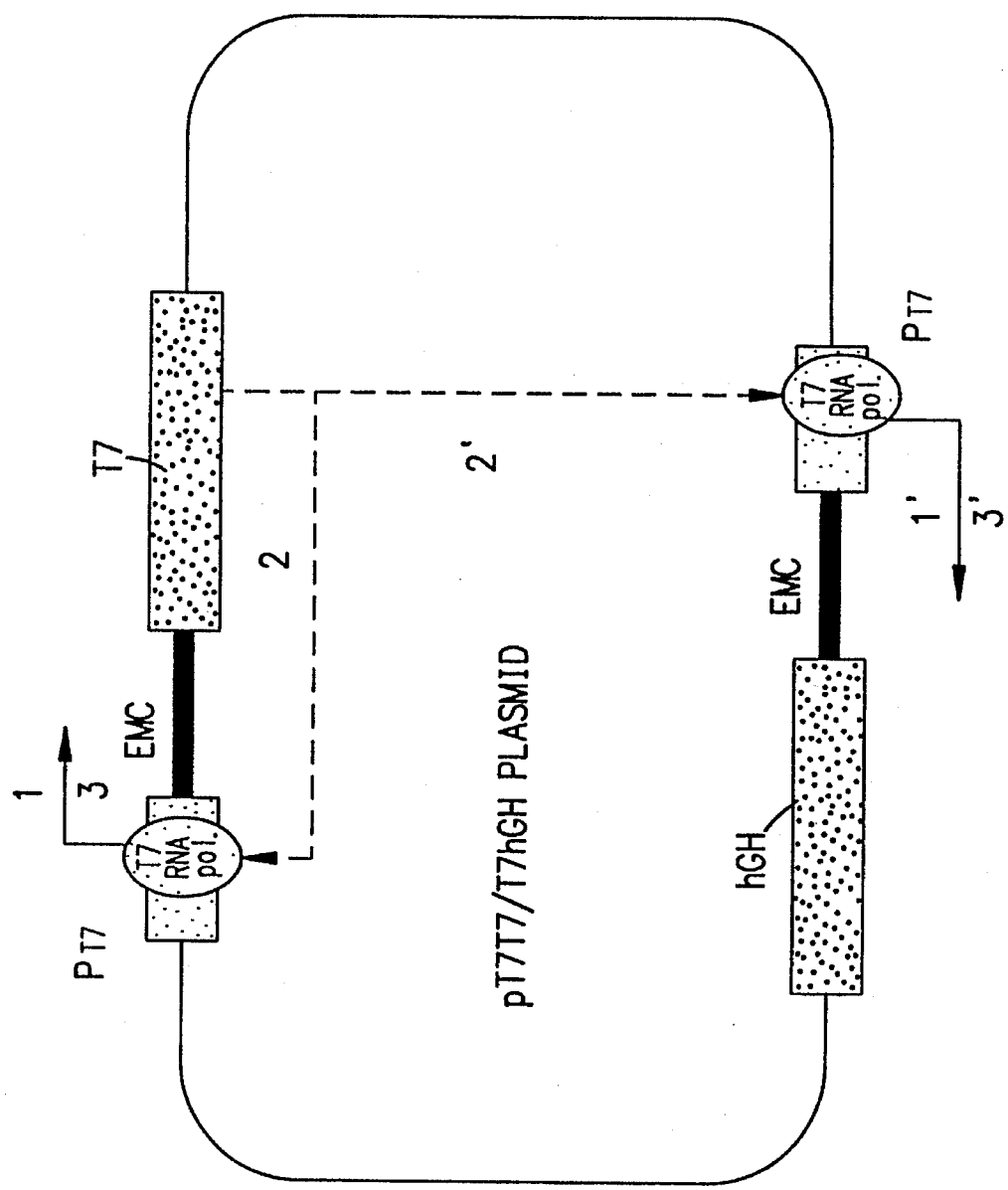

United States Patent [19]

Wagner et al.

[11] Patent Number: 5,591,601
[45] Date of Patent: Jan. 7, 1997

[54] DNA POLYMERASE GENE EXPRESSION SYSTEM UTILIZING AN RNA POLYMERASE CO-DELIVERED WITH THE GENE EXPRESSION VECTOR SYSTEM

[75] Inventors: Thomas E. Wagner, Albany; Xiaozhuo Chen; Yunsheng Li, both of Athens, all of Ohio

[73] Assignee: Ohio University Edison Animal Biotechnology Institute, Athens, Ohio

[21] Appl. No.: 62,657

[22] Filed: May 14, 1993

[51] Int. Cl.$^6$ ............................ C12N 5/16; C12N 15/18; C12N 15/85

[52] U.S. Cl. .................. 435/69.1; 435/69.4; 435/91.21; 435/91.31; 435/172.3; 435/240.2; 435/320.1; 536/23.1; 536/24.1; 536/24.5; 514/44

[58] Field of Search ..................................... 435/69.1, 183, 435/69.4, 91.31, 91.21, 172.3, 320.1, 240.1, 252.3, 254.11, 257.2, 240.2; 536/23.1, 24.1; 935/34, 36, 38, 39; 514/44

[56] References Cited

U.S. PATENT DOCUMENTS

| | | | |
|---|---|---|---|
| 4,952,496 | 8/1990 | Studier et al. | 435/91.41 |
| 5,126,251 | 6/1992 | Moss et al. | 435/69.1 |

FOREIGN PATENT DOCUMENTS

WO90/11092  10/1990  WIPO.

OTHER PUBLICATIONS

Gao et al. NAR (1993) 21:2867–2872. Provided as Biosis abstract Acc #:96063309.
Elroy–Stein et al. PNAS (1989) 86:6126–6130.
Gao et al. Cell. Biochem. Suppl. (17 Part E.) 1993, Abstract #206, S307 (Presented at a meeting held Apr. 12–18, 1993).
Fuerst et al. J Mol. Biol. 206 333–348 (1989).
Moss et al., 1990, "New mammalian expression vectors," Nature 348:91–92.
Deng et al., "High–Efficiency Protein Synthesis form T7 Rna Polymyerase in 3T3 Fibroblasts", Gene 109:193–201 (1991).
Dubendorff and Studier, "Creation of a T7 Autogene: Cloning and Expression of the Gene for Bacteriophage T7 RNA Polymerase under Control of its Cognate Promoter", J Mol Biol 219:61–68 (1991).

*Primary Examiner*—John L. LeGuyader
*Attorney, Agent, or Firm*—Pennie & Edmonds

[57] ABSTRACT

The present invention relates to a gene expression system in eukaryotic cells. In particular, it relates to a self-initiating and self-sustaining gene expression system utilizing an RNA polymerase prebound to a DNA construct before the introduction of the complex into cells. This system is capable of functioning in the cell cytoplasm without integration into the genome of host cells, and does not require host cell factors for initiation and maintenance of gene expression. Therefore, the invention has a wide range of applications in in vitro and in vivo gene expression, including gene therapy in resting cells.

38 Claims, 10 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:1:

GGAATTGTGA GCGGATAACA ATTCC 25

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: unknown ( i i ) MOLECULE TYPE: DNA ( x i ) SEQUENCE DESCRIPTION: SEQ ID NO:2:

CCCGATTTAC TAACTCCATG GACACGATTA ACATCGCTAA G 41

DNA POLYMERASE GENE EXPRESSION SYSTEM UTILIZING AN RNA POLYMERASE CO-DELIVERED WITH THE GENE EXPRESSION VECTOR SYSTEM

1. INTRODUCTION

The present invention relates to a gene expression system in eukaryotic cells. In particular, it relates to a self-initiating and self-sustaining gene expression system utilizing an RNA polymerase prebound to a DNA construct before the introduction of the complex into cells. This system is capable of functioning in the cell cytoplasm without integration into the genome of host cells, and does not require host cell factors for initiation and maintenance of gene expression. Therefore, the invention has a wide range of applications in in vitro and in vivo gene expression, including gene therapy in resting cells.

2. BACKGROUND OF THE INVENTION

2.1. EXOGENOUS GENE EXPRESSION

Advances in recombinant DNA technology have permitted the expression of exogenous foreign genes in eukaryotic cells. Foreign gene expression has not only facilitated studies of gene function and the production of properly processed gene products, it has also led to the possibility of correcting gene defects by introducing functionally active genes in gene therapy.

A number of gene delivery and expression systems have been developed and successfully used to express foreign genes in eukaryotic cells, and less satisfactorily, in animals. These systems consist primarily of a DNA delivery method and a DNA expression vector. DNA delivery methods include calcium phosphate precipitation (Wigler et al., 1979, Proc. Natl. Acad. Sci. USA 76:1373–1376), DEAE-dextran (Sompagnac et al., 1981, Proc. Natl. Acad. Sci. USA 78:7575–7578), lipofection (Felgner et al., 1987, Proc. Natl. Acad. Sci. USA 84:7413–7417), electroporation (Neumann et al., 1982, EMBO J. 7:841–845), retroviruses (Schimotohono et al., 1981, Cell 26:67–77), direct DNA injection (Benvensty et al., 1986, Proc. Natl. Acad. Sci. USA 83:9551–9555; Wolff et al., 1990, Science 247:1465–1468), specific receptor-mediated DNA uptake (Wu et al., 1988, J. Biol. Chem. 263:14621–14624; Wu et al., 1989, J. Biol. Chem. 264:16985–16987), and more recently, aerosol DNA delivery (Stribling et al., 1992, Proc. Natl. Acad. Sci. USA 89:11277–11281). Expression vectors are in general plasmid DNA containing a gene of interest linked to a regulatory sequence which controls the expression of the gene upon its introduction into a given cell.

Since these gene expression systems usually utilize eukaryotic or mammalian promoters to direct gene transcription, they require entry into host cell nuclei and integration of the exogenous DNA for expression. However, only a very small percentage of the cells which take up DNA contain the foreign DNA within the nuclei of the cells. This problem becomes even more pronounced when whole animals are the targets of foreign gene expression because cell division, which is required for nuclear deposition of the introduced DNA, does not always occur at as high a frequency in the cells of tissues as it does in cultured cell lines, making it difficult for exogenous DNA to integrate into non-dividing cells.

On the other hand, evidence has indicated that the cytoplasmic uptake of foreign DNA by cells and animals is efficient (Felgner et al., 1987, Proc. Natl. Acad. Sci. USA 84:7413–7417). And, in certain circumstances, the DNA introduced into the cells of whole animal tissues has been observed to remain in the cytoplasm up to several months (Wolff et al., 1990, Science 247:1465–1468).

2.2. BACTERIOPHAGE RNA POLYMERASE

Bacteriophage T7 RNA polymerase (RNAP) has been studied extensively in vitro and in vivo in bacteria and eukaryotic cells due to several of its unique biochemical characteristics. In particular, T7 RNAP is a single polypeptide enzyme capable of carrying out transcription with high promoter specificity and efficiency, without the involvement of any other cellular transcription factors (Davanloo et al., 1984, Proc. Natl. Acad. Sci. USA 81:2035–2039; Dunn et al., 1983, J. Mol. Biol. 166:477–535; Studier et al., 1990, Methods Enzymol. 185:60–89). For example, recombinant vaccinia viruses containing a T7 RNAP gene or a cell line which constitutively expresses T7 RNAP have been used to promote expression of genes of interest linked to T7 promoter in the cytoplasm of mammalian cells (Fuerst et al., 1986, Proc. Natl. Acad. Sci. 83:8122–8126; Fuerst et al., 1989, J. Mol. Biol. 206:333–348; Elroy-Stein et al., 1989, Proc. Natl. Acad. Sci. USA 86:6126–6130; Elroy-Stein et al., 1990, Proc. Natl. Acad. Sci. USA 87: 6743–6747). When a chloramphenicol acetyltransferase (CAT) gene was inserted into a T7 promoter-containing mammalian vector and transfected into a stable cell line which also expressed T7 RNAP, as high as 30% of cytoplasmic proteins was found to be the CAT enzymes in the transfected cells (Elroy-Stein et al., 1990, Proc. Natl. Acad. Sci. USA 87: 6743–6747). However, a major limitation of such a T7 gene expression system is that it must be performed in cell lines which also express the T7 RNAP gene, which is a bacterial gene not expressed endogenously in eukaryotic cells.

3. SUMMARY OF THE INVENTION

The present invention relates to a self-initiating, self-sustaining gene expression system in eukaryotic cells utilizing an RNA polymerase prebound to a DNA molecule, and its use in the expression of genes in in vitro cell lines and in in vivo tissues, including gene therapy. The unique components of this expression system allow gene transcription without requiring the involvement of host cell factors and without integrating into the host cell genome.

The present invention is based, in part, on Applicants' discovery of significant gene expression from a DNA construct complexed to T7 RNAP, which construct contains a T7 RNAP gene driven by a T7 promoter, and another nucleotide sequence encoding a functional or a reporter gene i.e. a gene of interest, under the control of a second T7 promoter (T7T7/T7-gene construct). One unique feature of the construct which distinguishes this system from other gene expression systems is that both the initiation and maintenance of gene expression depend upon the binding of T7 RNAP to DNA prior to the introduction of the construct into host cells. The complex of prebound RNAP to plasmid DNA is stable without detachment during entry into cells. Once the DNA-RNAP enzyme complex enters the cytoplasm of the cells, transcription is initiated immediately by the prebound T7 RNAP via the prebound T7 promoters in the plasmid. The subsequent production of T7 RNAP enzyme, in turn, triggers transcription of the functional/reporter gene as well as continued synthesis of additional T7 RNAP, thus it is both a self-initiating and a self-sustaining system. The transcription of both the T7 RNAP and the functional/reporter genes can be driven repeatedly by newly synthesized T7 RNAP in the cell cytoplasm without nuclear integration.

The human growth hormone (hGH) gene encoding a secretory protein, the chloramphenicol acetyltransferase (CAT) gene and the luciferase gene, both encoding intracellular enzymes have been expressed using the expression system of the invention in mouse and human cell lines, and in different mouse tissues in vivo. The expression system described herein provides a method for the efficient expression of cytoplasmically introduced genetic sequences encoding proteins, antisense RNA or ribozymes in a wide variety of host cells, including mitotically quiescent cells.

4. BRIEF DESCRIPTION OF THE DRAWINGS

Schematic presentation of self-initiation and positive feedback loop features of the T7T7/T7-gene expression system. A. Cotransfected, prebound T7 RNAP initiate transcription from T7 promoters ($P_{T7}$) on both T7T7 and T7hGH sequences (1 and 1'). EMC serves as cap independent sequence in translation for the T7 and hGH transcripts; B. newly synthesized T7 RNAPs replenish the polymerase pool in the cytoplasm of the transfected cells (2 and 2'); and C. maintenance of the T7 and hGH gene expression in the cells (3 and 3'). In this plasmid, hGH cDNA can be replaced to express other cDNA.

Figure 2:
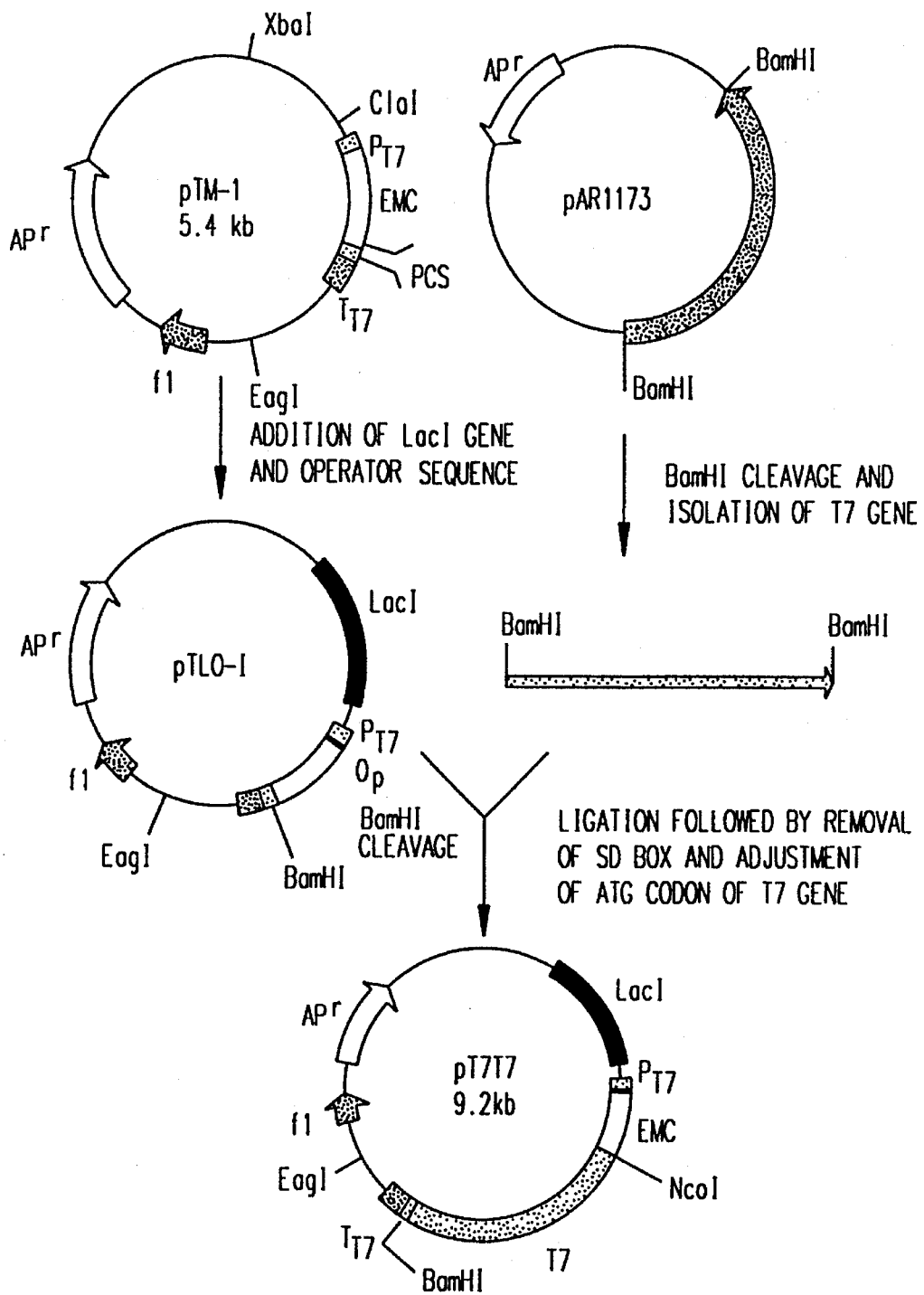

FIG. 2. Construction of pT7T7 plasmid. pTM-1 and pAR1173 were used as starting plasmids. pTM-1 contained a bacteriophage T7 ($\phi$10) promoter ($P_{T7}$), a capping independent (EMC) sequence which facilitated translation of uncapped transcripts, as well as a T7 transcription termination sequence ($T_{T7}$). Polycloning site (PCS) in pTM-1 contained several restriction sites for cDNA insertion. pAR1173 provided a T7 RNAP gene (Bam HI fragment). In pTLO-1, Lac I and Op represented the Lac I gene and the operator sequence, respectively.

FIG. 3. Structure of plasmids pT7hGH and pT7CAT. A. pT7hGH, B. PT7CAT. pT7hGH and pT7CAT were constructed using similar strategies. Both genes were individually inserted into pTM-I. NcoI site (5'-proximal one for PT7CAT) in both plasmids represented the junction of the EMC sequence and the inserted genes (hGH or CAT). ATG codon in the NcoI site represented the first amino acid residue for both hGH and CAT proteins. Internal restriction sites Bgl II for the hGH cDNA and NcoI for the CAT gene were used for restriction analysis to identify the inserted genes. pT7hGH and pT7CAT did not contain either Lac I or operator sequences.

Figure 4:
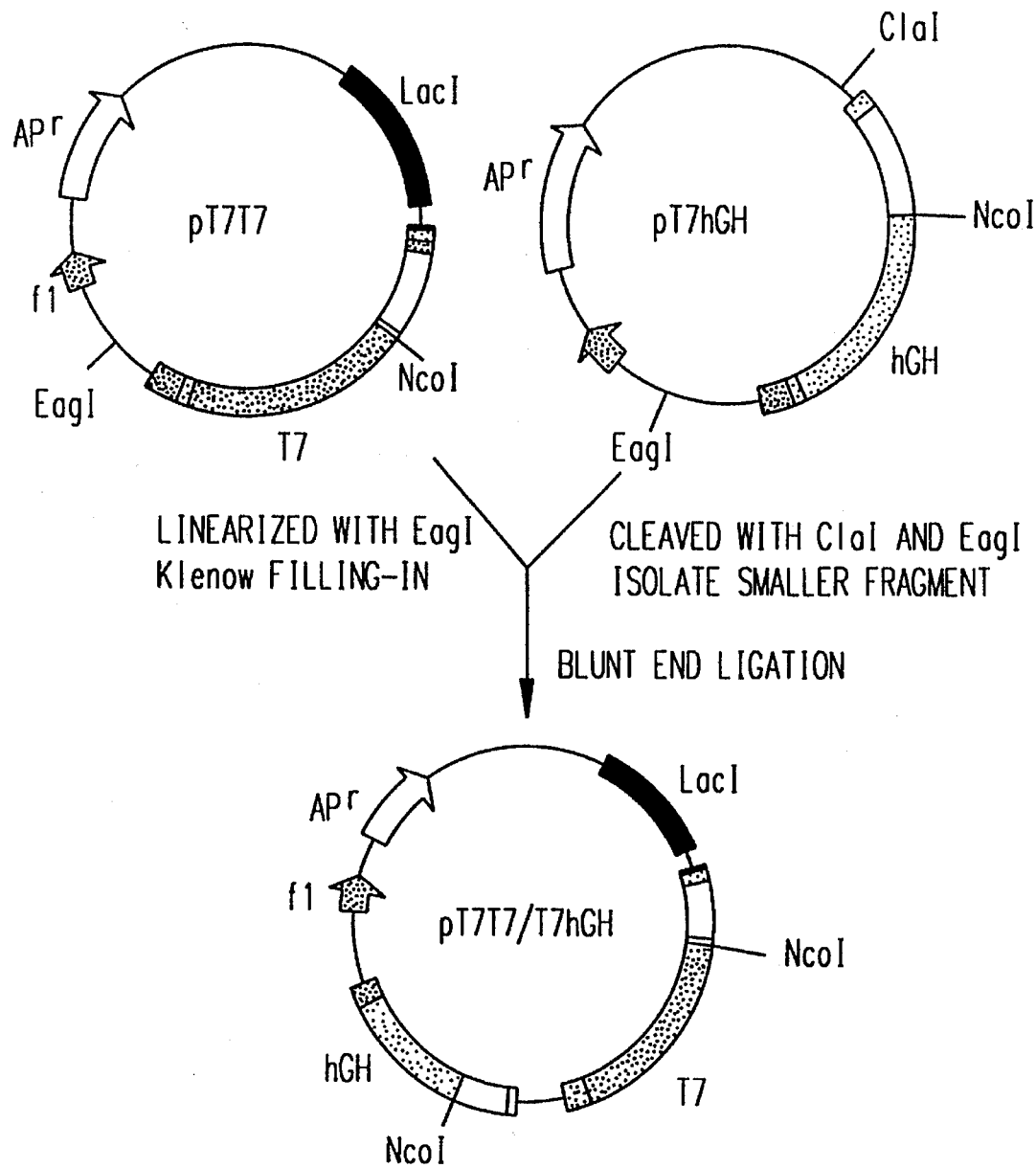

FIG. 4. Construction of pT7T7/T7hGH. Smaller ClaI/ EagI fragment from PT7hGH was isolated and inserted into EagI site of pT7T7 by a blunt end ligation. The orientation of the T7hGH fragment in pT7T7/T7hGH was the same as that of the T7T7 sequence. In this plasmid, T7hGH sequence had a structural arrangement similar to T7T7 except that the operator was absent from T7hGH sequence.

Figure 5:
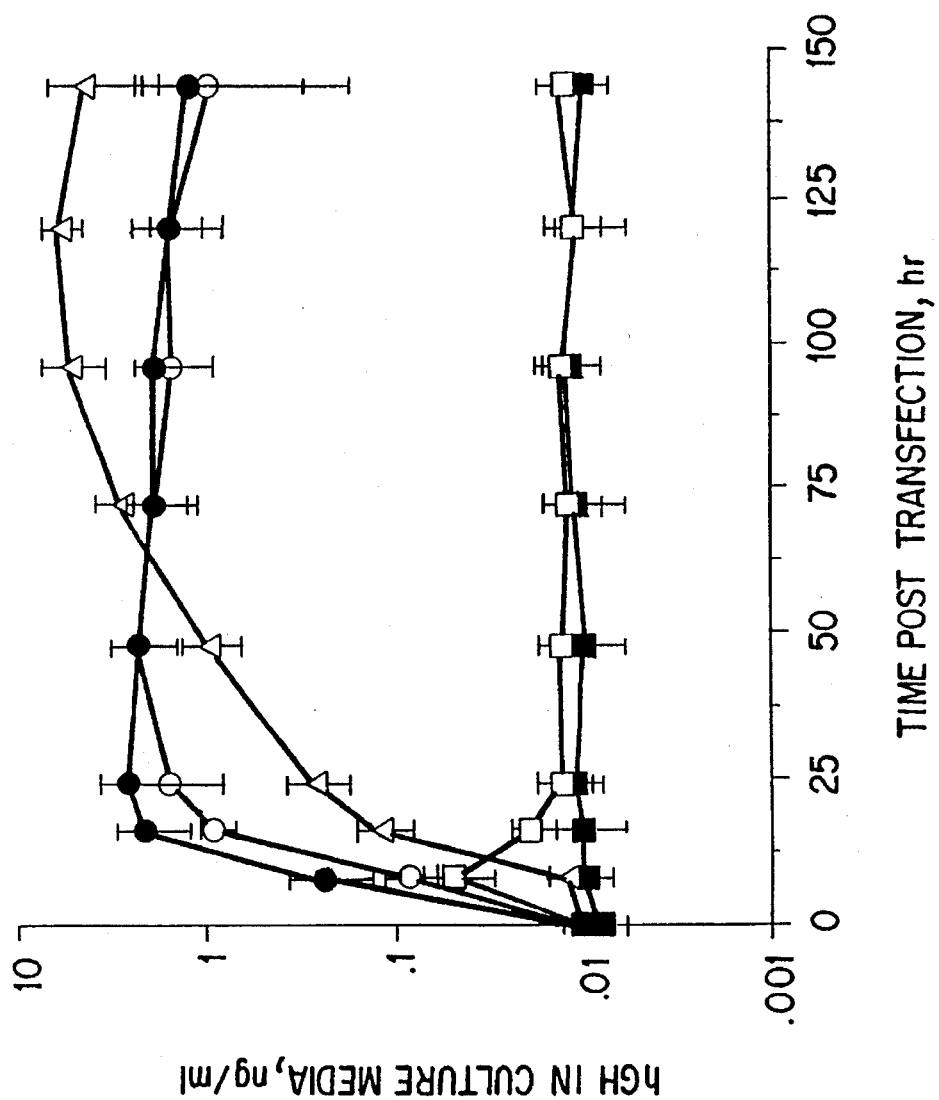

FIG. 5. Expression of hGH in mouse L cells transfected by T7hGH system. Mouse L cells were transfected by either pT7T7+pT7hGH (dual plasmids) or pT7T7/T7hGH (single plasmid) with prebound T7 RNAP as follows: One µg of plasmid DNA (0.5 µg+0.5 µg for dual plasmids) was coincubated with 125 U of T7 RNAP at room temperature for 10 minutes, 20 µl of lipofectin was mixed with the DNA-enzyme complexes to a final volume of 100 µl. Following 5 min room temperature incubation, the liposome-DNA-enzyme mixture was added to mouse L cells in a 6-well cell culture dish. Cell samples transfected by pT7T7/T7hGH alone, pT7hGH+T7 RNAP, or pMThGH (1 µg DNA/well) served as negative and positive controls, respectively. Each point in curves represented an average value of at least three individual measurements. Error bars represent standard deviations of the measurements. ■ pT7T7/T7hGH alone, □ pT7hGH+T7 RNAP, Δ pMThGH, ○ pT7T7+pT7hGH+T7 RNAP, and ● pT7T7/T7hGH+T7 RNAP.

Figure 6:
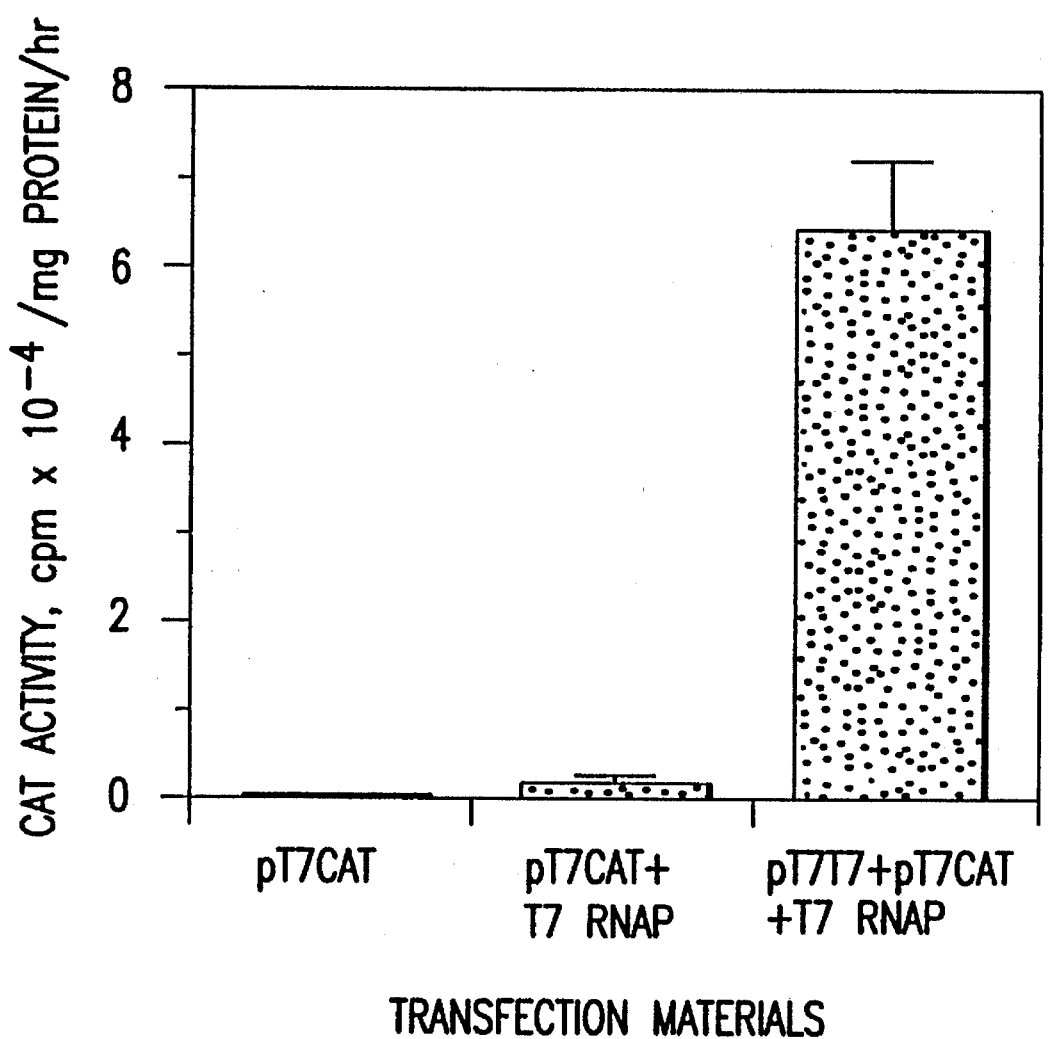

FIG. 6. Expression of the CAT gene in mouse L cells transfected with pT7T7+pT7CAT with prebound T7 RNAP. Transfection was performed the same way as described. 24 hours after the transfection, the cells were harvested and assayed for CAT activity. Cell samples transfected with either pT7CAT alone or pT7CAT with prebound T7 RNAP served as controls. Error bars represent standard deviations of the measurements.

Figures 7A, 7B:
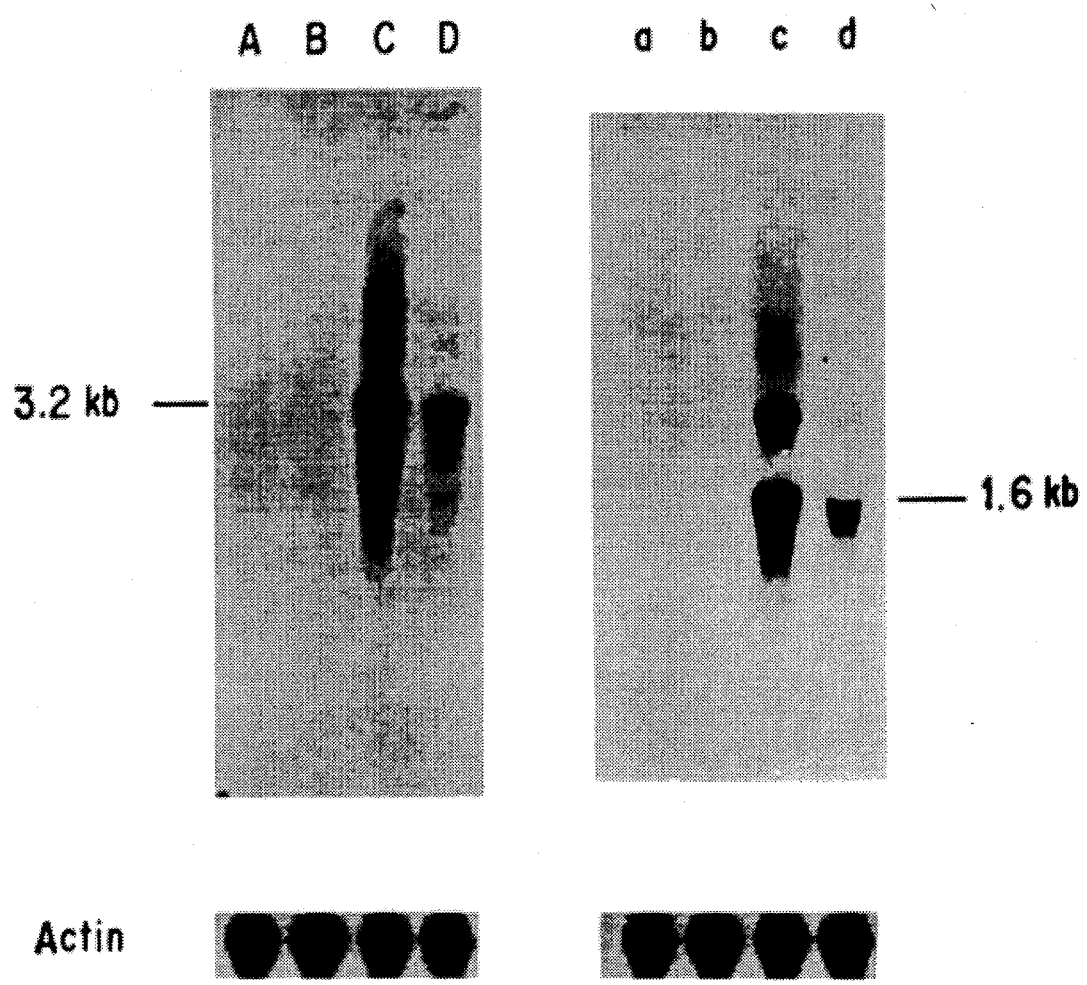

FIG. 7. Northern analysis of the T7 and hGH mRNA expressed by mouse L cells transfected by the T7 system. The cells were transfected by the T7 system, and total RNA was isolated. Following gel electrophoresis and transfer of resolved RNA on a membrane, the membrane was hybridized first with a 2.6 kbp $^{32}$P-labeled T7 probe, then by a 0.9 kbp hGH probe after stripping off the first T7 probe. Actin mRNA in each sample served as a RNA concentration reference. I. Northern blot using T7 probe. A=cells transfected by pT7T7/T7hGH, B=pT7hGH+T7 RNAP, A and B were isolated 24 hr after the transfection. C and D=pT7T7/T7hGH+T7 RNAP; sample C was isolated 24 hr post transfection, D=48 hr. II. Same membrane hybridized with a hGH probe. Lane order is the same as in 1.

Figure 8:
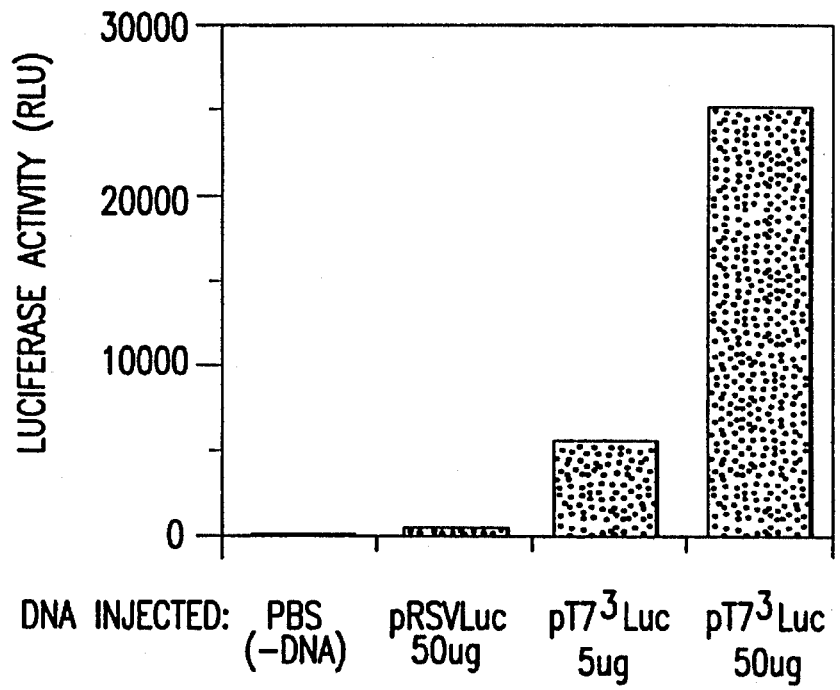

FIG. 8. Luciferase expression in mouse tail connective tissues by injection of pT7T7/T7Luc plasmid DNA. Different amounts of plasmid DNA pT7T7/T7Luc, were complexed with T7 RNAP in test tubes, and injected into the tail connective tissues BALB/c mice of 1–2 months of age. Twenty four hours post injection, injected tail tissues were homogenized using 300 µl Luciferase Lysis Buffer, followed by centrifugation to precipitate cell debris. Five µl of the cell lysate from each sample was used for luciferase assays.

Figure 9:
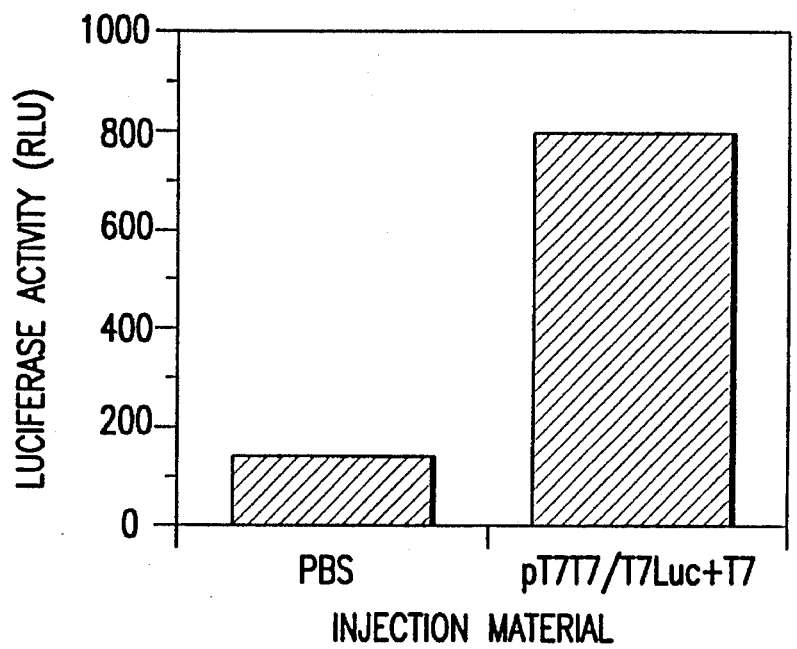

FIG. 9. Luciferase expression in mouse leg muscles by injection of pT7T7/T7Luc plasmid DNA. One hundred µl of solution, which contained either PBS or 25 µg pT7T7/T7Luc complexed with T7 RNAP, were injected into mouse hind leg muscles using 25 G needles. Twenty four hours after injection, the injected muscles were isolated, homogenized, and assayed for luciferase activity.

Figure 10:
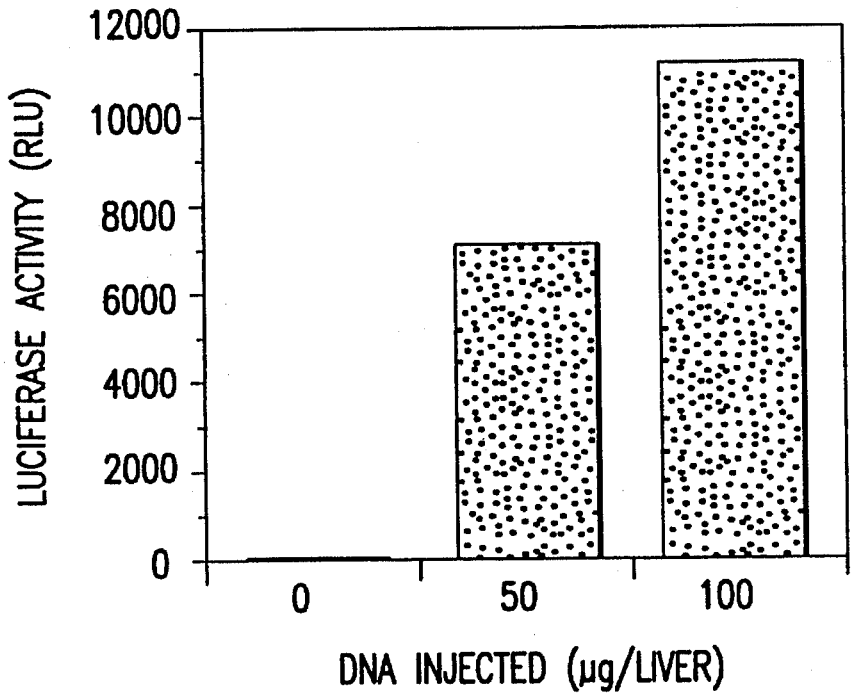

FIG. 10. Luciferase expression in mouse livers by direct DNA injection. One hundred µl of DMEM solution, which contained 50 or 100 µg of pT7T7/T7Luc DNA complexed with T7 RNAP, were injected into one lobe of BALB/c mouse livers. Twenty hours after the injection, mouse livers were removed, homogenized, and assayed for luciferase activity.

Figure 11:
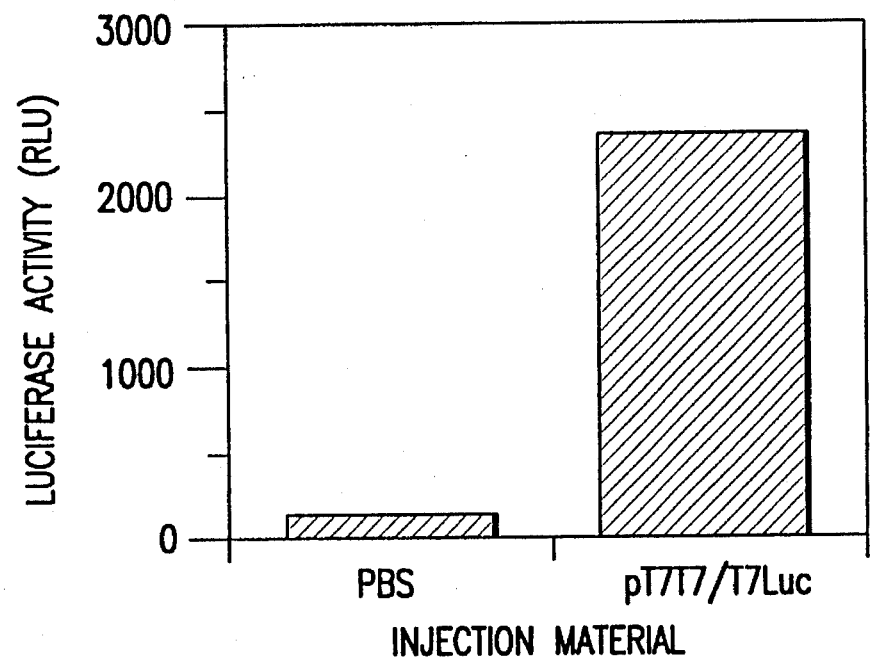

FIG. 11. Luciferase expression in mouse brains by injection of pT7T7/T7Luc plasmid DNA. Fifty µl of solution, which contained either PBS or pT7T7/T7Luc DNA-T7 RNAP complex, were injected into the brain tissues of BALB/c mice of 20 days of age. Sixteen hours after the injection, brain tissues were removed and lysed into 400 µl of Luciferase Lysis Buffer. Ten µl of cell lysates were assayed for luciferase activity as described previously.

Figure 12:
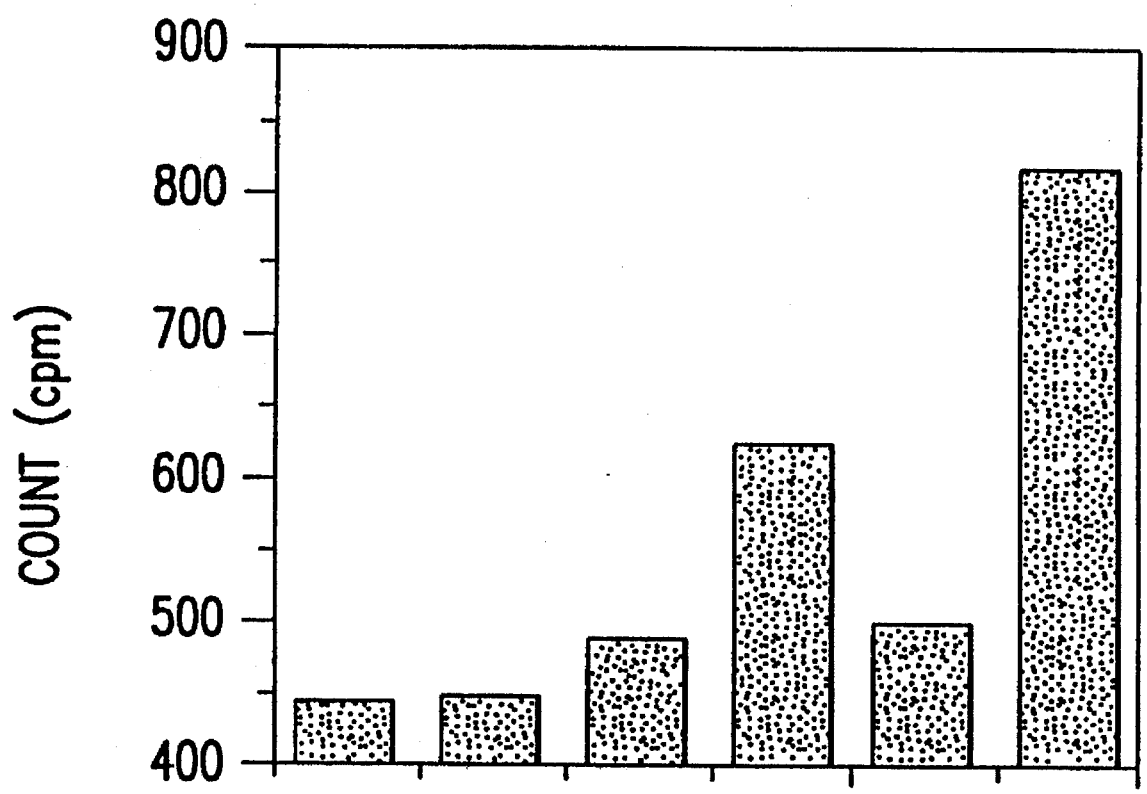

FIG. 12. Human growth hormone expression in mouse brain tissues and in cerebrospinal fluids. Fifty to 80 µl of solution, which contained either PBS, pT7T7/T7hGH+T7 RNAP, or pT7T7/T7hGH+T7 RNAP+lipofectin, were injected into the cerebrospinal fluid from the top of the head of mice of 20 days of age. Twenty hours after the injection, cerebrospinal fluids and brain tissues from the injected mice were isolated, homogenized, and assayed for hGH activity by an hGH RIA. CSF=cerebrospinal fluid, BT=brain tissue.

5. DETAILED DESCRIPTION OF THE INVENTION

The present invention relates to a gene expression system in eukaryotic host cells. This system is different from other expression systems because it relies on the binding of an RNA polymerase to a DNA molecule constructed to contain its cognate promoter and the RNAP coding sequence, and a functional/reporter gene also driven by the same cognate promoter, prior to cell transfection (FIG. 1). This arrangement creates a potential positive feedback loop for the expression of the RNAP gene. Once this DNA-enzyme complex is introduced into eukaryotic cells, the transcription of the RNAP and the functional/reporter genes is initiated by the prebound RNAP. The prebound RNAP, which is responsible for the initiation of the expression of both the RNAP and the functional/reporter genes, is replenished by translation of newly synthesized RNAP. This expression system has been designed in such a manner that the expression of the functional/reporter genes can occur in the cytoplasm and does not require any nuclear involvement.

The invention is discussed in more detail in the subsections below, solely for purposes of description and not by way of limitation. For clarity of discussion, the specific procedures and methods described herein are exemplified using specific genes and cell lines; they are merely illustrative for the practice of the invention. Analogous procedures and techniques are equally applicable to all genes and tissues.

5.1. ISOLATION OF A PROTEIN CODING SEQUENCE

The expression system of the invention may be used to express any gene of interest in eukaryotic cells. An isolated gene sequence may be inserted into a plasmid in a manner similar to that described in Section 6.1.3., infra. For the isolation of a gene sequence encoding a gene product of interest, messenger RNA (mRNA) may be obtained from cell sources that produce the protein, whereas its genomic sequences may be obtained from any cell source. Genetically-engineered microorganisms or cell lines containing the protein coding sequence may be used as a convenient source of DNA for this purpose.

Either cDNA or genomic libraries may be prepared from the DNA fragments generated using techniques well known in the art. The fragments which encode a specific protein may be identified by screening such libraries with a nucleotide probe homologous to a portion of the protein which is based on amino acid sequence information obtained from the purified protein. Alternatively, an antibody probe may be used to screen a library generated by expression cloning methods such as λgt11 (Young and Davis, Proc. Natl. Acad. Sci. U.S.A. 80:1194–1198). Where a partial sequence of the gene of interest is known, PCR (polymerase chain reaction), LCR (ligase chain reaction) or the like can be utilized to generate and identify clones. (Innis et al., 1990, PCR Protocols, Academic Press Inc., New York) Although portions of the coding sequence may be utilized for cloning and expression, full length clones, i.e, those containing the entire coding region for a protein, may be preferable for expression. To these ends, techniques well known to those skilled in the art for the isolation of DNA, generation of appropriate restriction fragments, construction of clones and libraries, and screening recombinants may be used. (See, for example, the techniques described in Maniatis et al., 1989, Molecular Cloning, A Laboratory Manual, Cold Spring Harbor Laboratory, N.Y.)

Regardless of the method chosen to identify and clone a specific coding sequence, expression cloning methods may be utilized to substantially reduce the screening effort. Recently, a one step procedure for cloning and expressing antibody genes has been reported (McCafferty et al., 1990, Nature 348:552–554; Winter and Milstein, 1991, Nature 349:293–299). Based on this technology, any gene may likewise be cloned directly into a vector at a site adjacent to the coat protein gene of a bacteriophage such as λ or fd. The phage carrying the gene of interest expresses the fusion protein on its surface so that columns containing a specific antibody can be used to select and isolate phage particles with binding activity. A commercially available expression cloning system utilizing Lambda-Zap-bluescript may also be used for the cloning and antibody screening of cDNA libraries (Stratagene, La Jolla, Calif.). Transient gene expression systems may be utilized to identify the correct gene of interest. For example, the COS cell system (e.g., Gerard & Gluzman, 1986, Mol. Cell. Biol. 6(12) 4570–4577) may be used.

Due to the degeneracy of the nucleotide coding sequences, other DNA sequences which encode analogous amino acid sequences for any known gene may be used in the practice of the present invention for the cloning and expression of its gene product. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Oligonucleotide sequences can be used to increase the copy number of a unique gene sequence by the polymerase chain reaction. This approach would provide for more specific probes than that obtained using degenerate oligonucleotides.

In addition, other DNA sequences containing structural modifications but without substantial alteration of the biologic activities of the encoded protein may also be used in the practice of the invention. Such modifications include but are limited to additions, deletions or substitutions of amino acid residues in a protein to create additional processing sites and/or elimination of glycosylation sites. For example, the removal of N-linked glycosylation sites in certain proteins results in reduced glycosylation on the expressed products which are particularly useful in yeast expression systems.

5.2. ANTI-SENSE RNA AND RIBOZYMES

Also within the scope of the invention is the expression of oligo-ribonucleotide sequences, that include anti-sense RNA and ribozymes that function to inhibit the translation of a variety of mRNA. Anti-sense RNA acts to directly block the translation of mRNA by binding to targeted mRNA and preventing protein translation, either by inhibition of ribosome binding and/or translocation or by bringing about the nuclease degradation of the mRNA molecule itself.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of mRNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complimentary oligonucleotides, using ribonuclease protection assays.

Both anti-sense RNA and ribozymes may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into the expression system of the invention.

Various modifications to the DNA molecules may be introduced as a means of increasing intracellular stability and half-life. Possible modifications include but are not limited to the addition of flanking sequences of ribo- or deoxynucleotides to the 5' and/or 3' ends of the molecule or the use of phosphorothioate or 2' O-methyl rather than phosphodiesterase linkages within the oligodeoxyribonucleotide backbone.

5.3. SELF-INITIATING AND SELF-SUSTAINING GENE EXPRESSION SYSTEMS

According to one aspect of the present invention, a self-initiating and self-sustaining gene expression system may be constructed by binding a RNA polymerase to a DNA construct containing a cognate promoter of the RNA polymerase operably linked to a nucleotide sequence encoding the RNA polymerase. Operably linked is used herein to describe the transcription from the promoter by the RNA polymerase in the host cell to produce functional RNA transcripts that can be translated to the RNA polymerase protein. The gene construct that operably links the RNA polymerase encoding sequence to a promoter sequence recognized by the same RNA polymerase is referred to hereinafter as an autogene (Dubendroff and Studier, 1991, J. Mol. Biol. 219:61–68, for the orgin of the "autogene" term and an example of a T7 RNA polymerase autogene).

The RNA polymerase of the present invention should be capable of carrying out transcription in the intended eukaryotic host cell. It is preferred that the RNA polymerase is not complex in composition, e.g., composed of multiple subunits, and should have sufficiently high affinity for its cognate promoter so that the complex is maintained during introduction into host cells. A functional RNA polymerase made up of no more than two subunits is preferable. More preferable is a RNA polymerase composed of only homomers. Most preferable is a RNA polymerase that is a small single unit enzyme, that does not require host cell factors for activity, that recognizes its cognate promoter sequence with a high degree of specificity, and that is highly active. Examples of RNA polymerases suitable for use in the present invention include, but are not limited to, the RNA polymerases of the T7, T3, SP6, or K11 bacteriophages or of the RNA polymerases of mitochondria. (See Chamberlin and Ryan, 1983, Dietz et al, 1990, Mol. Gen. Genet. 221:283–286; Schinkel and Tabak, 1989, Trend Genet. 5:149–54).

An autogene construct of the present invention generally includes five components linked in the following 5 ' to 3' orientation: a cognate promoter of the RNA polymerase, a sequence encoding an 5' untranslated RNA (UTR), a sequence encoding the RNA polymerase, a sequence encoding a 3'-UTR, a cognate transcription terminator of the RNA polymerase. These parts are linked such that transcription by the RNA polymerase from the cognate promoter would initiate at the 5'-end of the 5'-UTR sequence, proceed through the sequences encoding the 5'-UTR, the RNA polymerase and the 3'-UTR sequences, and terminate in the cognate transcription terminator. A transcript produced from such a autogene construct in the eukaryotic host cell would contain a RNA that has the 5'-UTR sequence at its 5'-end, the RNA polymerase sequence in its middle, and the 3'-UTR sequence at its 3'-end.

The cognate promoter sequence can be a promoter sequence cloned from the genome encoding the RNA polymerase. The location of a promoter can be identified by approaches and methods well known in the art, including DNase foot printing of the RNAP bound genome DNA, mutational analysis, etc. Alternatively, where the sequence of a cognate promoter is known, the promoter sequence can be synthesized. It may be advantageous to modify the cognate promoter by attaching at its 3'-end a bacterial operator sequence such as the lac operator. The operator sequence may serve to reduce the toxicity of constructs containing the autogene in the bacteria host. It would be advantageous that the operator is a short sequence. Preferably the operator is no longer than 50 basepairs. Most preferably the operator is no longer than 25 basepairs.

The cognate promoter, unmodified or modified, is operably linked at its 3'-end to the 5'-end of the 5'-UTR encoding sequence such that the transcription by the RNA polymerase from the cognate promoter would initiate RNA synthesis at the beginning (e.g. 5'-end) of the 5'-UTR sequence.

The 5'-UTR sequence encodes a RNA that can enable the formation of translational initiation complex in the eukaryotic host cell without the need for the RNA to be "capped" at it's 5'-end. (Kozak, 1983, Microbiol. Rev. 47:1–45). Preferably, the 5'-UTR sequence encodes a RNA sequence from the 5' untranslated region of a picornavirus, such as encephalomyocarditis (EMC) virus, polio virus, mengo virus, etc. Most preferably, the 5'-UTR sequence encodes the 5' untranslated region of the EMC virus RNA (see Elroy-Stein et al., 1989, Proc. Nat. Acad. Sci. USA 86:6126–6130). In order to reduce the toxicity of autogene constructs in bacterial host, it may be advantageous to delete or mutate any fortuitous "Shine and Delgarno" sequences present at the 3'-end of the 5'-UTR sequence.

According to the present invention, the 3'-end of the 5'-UTR sequence is linked with the 5'-end of the RNA polymerase-encoding sequence. The RNA polymerase encoding sequence may be obtained by cloning from an appropriate genome. Approaches and methods for cloning RNA polymerase encoding sequences are well known in the art. They include the use of nucleotide probes derived from purified peptides of the RNAP or nucleotide probes from related RNAP to probe genomic or cDNA libraries or to generate clones using PCR, LCR etc. techniques. Alternatively, where the amino acid or nucleotide sequence of a desired RNA polymerase is known, the RNA polymerase encoding sequence may be synthesized according to the genetic code, using the codon choices most preferred by the host cell which is to express the autogene.

It may be advantageous, where appropriate, to modify the 5'-end of the RNA polymerase encoding sequence to prevent any out-of-frame (relative to the RNA polymerase coding sequence) AUG codons from being formed as a result of linking the polymerase encoding sequence to the 3'-end of the 5'-UTR sequence. The necessary modifications may involve methods well known in the art including site-specific mutagenesis, addition or deletion of short sequences, and/or any other type of sequence manipulations. According to the present invention, the 5'-end of the 3'-UTR encoding sequence is linked to the 3'-end of the sequence encoding the RNA polymerase. The 3'-UTR encoding sequence should encode a RNA sequence that would stablize the autogene transcript in the eukaryotic host cell. Sequences that could serve such a function include those encoding the 3' untranslated RNA sequences of histone genes, or a polyadenylate nucleotide tract, commonly known as polyA tracts. Where a histone 3' untranslated RNA sequence is used as the 3'-UTR of an autogene construct, it is preferable that the source of the histone gene sequence be the eukaryotic host cell which is to express the autogene. Where a polyA encoding sequence is used as the 3'-UTR sequence in the autogene construct, the sequence can be synthesized. The length of the polyA tract encoded by the 3'-UTR sequence preferably is longer than 25 nucleotides and shorter than 250 nucleotides. A sequence encoding a polyA tract between 40 to 50 nucleotides in length is most preferred.

According to the present invention, the cognate transcription terminator sequence should be attached immediately 3' of the sequence encoding the 3'-UTR. The terminator sequence can be cloned from the genome encoding the RNA polymerase. The approaches and methods for cloning such terminator sequences are well known in the art and include physical mapping the 3' end of RNA transcripts by sequencing, RNase protection, etc. or genetic mapping by mutagenesis, deletion analysis, etc. Alternatively, where the sequence of a cognate terminator is known, the sequence can be synthesized.

In various embodiments of the present invention the RNA polymerase may be composed of several different proteins. In such instances, the present invention may be practiced by constructing an autogene encoding each of the heteromeric proteins, prebinding RNA polymerase to each autogene construct, and introducing simultaneously the protein-DNA complex for every subunit of the RNA polymerase into the host cell. Where the RNA polymerase is composed of few subunits, it may be advantageous to have a single DNA construct contain all the RNA polymerase autogenes.

In another aspect of the present invention, the self-initiating and self-sustaining gene expression system may be used to express other gene products including proteins, anti-sense molecules or ribozymes in eukaryotic host cells. Such gene products may be expressed by introducing into the eukaryotic host cell DNA containing gene constructs encoding the desired gene products together with DNA encoding the RNA polymerase autogene(s) prebound with the RNA polymerase, in which the gene construct encoding a desired gene product is under the control of a cognate promoter of the RNA polymerase.

According to the present invention, the construction of the gene construct encoding a desired gene product is identical to that of an autogene, except the sequence encoding the desired gene product replaces that encoding the RNA polymerase. That is the gene construct comprises of the same five parts linked in the same 5' to 3' order: a cognate promoter of the RNA polymerase, a sequence encoding a 5'-UTR, a sequence encoding the desired gene product, a sequence encoding a 3'-UTR, a cognate transcription terminator of the RNA polymerase. Where the desired gene product is an antisense RNA or ribozyme, the DNA sequences encoding the 5'-UTR and 3'-UTR may be advantageously omitted from the gene construct.

In addition, a single DNA construct containing both an autogene and a gene of interest under the control of two copies of the same cognate promoter is also within the scope of the invention. A single unit expression system may be more efficient for introduction into host cells than a dual system composed of two separate plasmids.

A plasmid containing a gene construct of the present invention may include a selectable marker for propagation of the construct in bacteria. Such selectable markers may contain an antibiotic resistance gene, such as those that confer resistance to ampicilin, kanamycin, tetracycline, streptomycin, or chloramphenicol, and the like. Further, a plasmid containing an autogene construct of the present invention may encode a bacterial expressible repressor gene, wherein the encoded repressor recognizes the operator sequence modifying the RNA polymerase promoter of the autogene. Examples of applicable repressor genes include those of the lactose, histidine, tryptophane operons, and the like.

A unique feature of the present invention is the ability to prebind RNAP to DNA prior to transfection. An RNAP having an affinity for DNA sufficient to allow its binding during entry into cells may be used for the practice of the invention. In fact, any DNA binding protein with such affinities may be used for this aspect of the invention. Conventional techniques, e.g. calcium phosphate precipitation, lipofection, electroporation, DEAE-transfection, and the like may be used to introduce the complex into host cells.

5.4. USES OF SELF-INITIATING AND SELF-SUSTAINING GENE EXPRESSION SYSTEMS

The present invention relates to a gene expression system possessing a number of unique characteristics. This system contains all necessary components for gene expression without the involvement of host cell factors, thus it is both self-initiating and self-sustaining. As a result, this system may provide for cell-type independent gene expression, as evidenced by the comparable expression efficiency of several genes in both human and mouse cells (see Example 6, infra).

In addition, gene expression is rapid because it does not require the entry of the DNA into the cell nuclei for the initiation of transcription. The cytoplasmic location of its site of action also provides for a safety feature which reduces the possibility of its integration into the host cell genome at a site adjacent to and thereby activating a dormant gene such as an oncogene. Furthermore, unlike retroviral vectors, even if DNA integration occurred, the exogenous promoter used would not be activated by eukaryotic transcription proteins. The only RNAP capable of activating the promoter sequence to initiate transcription is synthesized in the cell cytoplasm, and would not be able to gain access to the nucleus for binding to its cognate promoter because it lacks any nuclear translocation signal.

This expression system encompasses a variety of applications. For example, it is especially suitable for expressing genes in a specific cell type where appropriate promoters for that cell type are unavailable. It is also useful in vitro for the transient expression of a newly cloned gene for confirmation of the identity of its encoded gene product as well as the rapid production of high amounts of proteins for use in immunization of animals for the generation of specific antibodies. In this regard, the present invention may be used to introduce exogenous genes into cells and tissues in vivo for transient expression of the gene product to elicit an antigen-specific host immune response. The short-term nature of gene expression may be ideal for its use as a vehicle for in vivo immunization of a host to an antigen.

A major impediment in the current attempts of gene therapy is the integration of foreign genes in non-dividing eukaryotic host cells. The ability of the present system to permit gene expression in the cell cytoplasm circumvents this potential problem, as gene expression can be achieved in quiescent cells. However, as the DNA construct is gradually degraded in the cytoplasm or diluted in number when cells divide over time, the present invention is also self-limiting. The self-limiting nature of this expression system is particularly suitable for use in settings where gene expression is desirable only temporarily or transiently. For example, the present invention may be used to target lymphokines genes to tumor sites in vivo for the in situ activation of cytotoxic lymphocytes to mediate tumor cytolysis. Since the expression of the exogenous genes is transient, the uptake of DNA by cells not lysed in the process would not eventually induce permanent and sustained synthesis of lymphokines leading to potentially deleterious consequences, such as autoimmunity.

The present invention encompasses an expression system used as a single unit or as a dual system. A single-unit system includes the RNAP gene and a gene of interest within the same DNA construct prebound to RNAP. A dual system includes an autogene containing a RNAP prebound by RNAP and a separate plasmid containing a gene of interest driven by the same cognate RNAP promoter also prebound by RNAP. In many circumstances, it is most convenient to introduce a single DNA construct into host cells. However, the two plasmids systems are particularly useful in settings where it is desirable to adjust the ratio of the expressed RNAP and the gene product of interest by providing different ratios of the two plasmids. In this way, the system prevents uncontrolled expression of one protein over the other, especially if the RNAP is synthesized at a much faster rate than the gene of interest.

The expression system may be complexed with RNAP and suspended in saline, PBS, serum free media or any aqueous solution suitable for in vivo administration. The solution may be injected into an animal, including a human, intravenously, intramuscularly, intracranially, subcutaneously or directly into a tissue or organ. The DNA-RNAP complex may be injected alone, encapsulated by liposomes or linked to any carrier molecules capable of translocating the complex across the plasma membrane. For in vivo administration, the expression system may be injected in the dose range of 0.01–100 mg/kg. If the gene product of interest is desired to be secreted into the bloodstream, the complex may be injected intravenously to cause endothelial cell uptake and release of the gene product directly into the circulation.

6. EXAMPLE: T7 RNA POLYMERASE PREBOUND TO DNA DIRECTS GENE EXPRESSION IN CULTURED CELL LINES

6.1. MATERIALS AND METHODS

6.1.1. ENZYMES

Bacteriophage T7 RNAP (50 U/ul), restriction endonucleases, and the Klenow fragment were purchased from New England BioLabs.

6.1.2. CELLS AND PLASMIDS

Mouse L and human HepG2 cells were maintained in DMEM supplemented with 10% Nu serum or 10% calf serum (growth media), respectively. E. coli DH5α was from Bethesda Research Laboratories. E. coli HMS174 with pLysE (Studier et al., 1990, Methods Enzymol. 185:60–89; Studier, 1991, J. Mol. Biol. 219:37–44); plasmid pAR1173 (Davanloo et al., 1984, Proc. Natl. Acad. Sci. USA 81:2035–2039), which contains a gene coding for T7 RNAP, and pATUO-1 (Dubendorff and Studier, 1991, J. Mol. Biol. 219:61–68), which contains a Lac I gene, were provided by Dr. Studier. Plasmid pTM-I (Moss et al., 1990, Nature 348:91–92) was from Dr. Moss' laboratory. Plasmid phGH (Martial et al., 1979, Science 205:602–607) was from Dr. Goodman's laboratory. Plasmid pBLCAT (Luckow and Schutz, 1987, Nucleic Acids Res. 15:5490), which contains a CAT gene, was obtained from Dr. T. Coleman; and pMThGH, which contains hGH cDNA (Martial et al., 1979, Science 205:602–607) driven by a mouse metallothionein I promoter (Brinster et al., 1981, Cell 27:223–231), was constructed in our laboratory. The bacteria were grown in LB medium with appropriate antibiotics.

6.1.3. CONSTRUCTION OF PLASMIDS pTM-I, a cytoplasmic expression vector which contains a T7 promoter connected to at its 3' end an EMC capping independent sequence (Moss et al., 1990, Nature 348:91–92), was linearized with restriction enzyme Bam HI. A 2.6 kbp Bam HI fragment of pAR1173 containing a T7 gene was inserted into pTM-I vector by ligation. The ligation products were subsequently transformed into E. coli strain DH5α. However, 100% of the recombinant clones were found to have T7 gene inserted in an orientation opposite to that of the promoter's (which formed a T77T construct, not T7T7), suggesting that T7T7 construct was lethal to host bacteria (Studier, 1991, J. Mol. Biol. 219:37–44; Dubendorf and Studier, 1991, J. Mol. Biol. 219:61–68; Dubendorff and Studier, 1991, J. Mol. Biol. 219:45–59). Several steps were subsequently taken to reduce the toxicity to bacterial hosts resulted from the expression of the T7 gene, while maintaining the ability of the construct to be expressed in eukaryotic cells.

First, a 1.6 kbp EagI/EcoNI Lac I gene which encodes a repressor was isolated from pAUTO-1 and inserted into ClaI and XbaI sites of pTM-I by a blunt-end ligation (FIG. 2). In addition, an operator sequence, GGA ATT GTG AGC GGA TAA CAA TTCC (25 mer) (SEQ. ID NO:1), which provides the binding site for Lac I repressor, was inserted immediately 3' to the T7 promoter sequence (as shown in pTLO-1 in FIG. 2) where the operator was shown to have the maximal suppression of T7 promoter activity (Dubendorff and Studier, 1991, J. Mol. Biol. 219:45–59). As a second step to further reduce the cytotoxicity, the Shine-Dalgarno sequence (S-D box) of the T7 gene was removed from the gene to reduce unwanted translation of T7 mRNA which was generated as a result of a leaky Lac I suppression (FIG. 2). Oligonucleotide CCC GAT TTA CTA ACT <u>CCA TGG</u> ACA CGA TTA ACA TCG CTA AG (41 mer) (SEQ. ID NO:2) was used as a primer for deletion of S-D box sequence using a phagemid mutagenesis method (Kunkel, 1985, Proc. Natl. Aca. Sci. USA 82:488–492; Kunkel et al., 1987, Methods Enzymol. 154:367–382). In addition, an NcoI site (CCATGG, as underlined in the oligonucleotide) was added to the T7 gene. A 2.6 kbp NcoI/BamHI modified T7 fragment was inserted into the gap between the NcoI and BamHI sites of pTM-I in such a manner that the optimized translation of the T7 gene would be initiated from the ATG in the NcoI site (Brinster et al., 1981, Cell 27:223–231) (FIG. 2). However, this modification altered the second amino acid residue of T7 RNAP from an Asn (AAC) to an Asp (GAC). Finally, the constructed pT7T7 was transformed into and prepared from HMS174 cells which contained a plasmid pLysE encoding a T7 lysozyme, a T7 RNAP inhibitor. All the mutations described herein were confirmed by DNA sequencing (Sanger et al., 1977, Proc. Natl. Acad. Sci. USA 76:4350–4354).

Figure 3A:
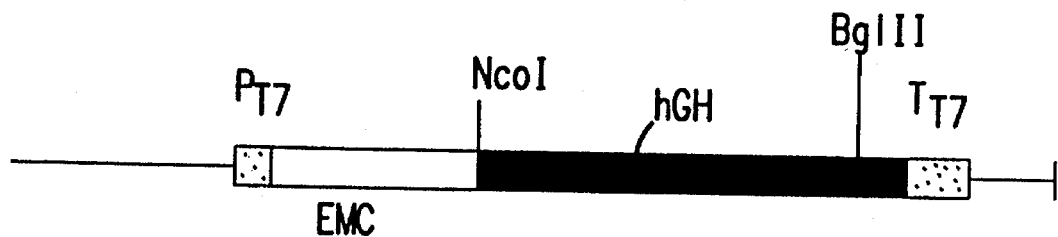

Construction of pT7hGH was simpler than that of pT7T7 since hGH is not toxic to the bacterial hosts. pTM-I was linearized with SmaI in the polycloning site. A 0.9 kbp Hind III fragment of an hGH cDNA was isolated from plasmid phGH, 5' protruding ends of the fragment were filled by Klenow fragment and dNTPs, and was inserted into pTM-I by a blunt-end ligation. With a deletion mutation, the reading frame of the hGH sequence was adjusted in a similar manner as for PT7T7 so that the ATG in NcoI site serves as the first codon for the hGH cDNA (FIG. 3A).

Figure 3B:
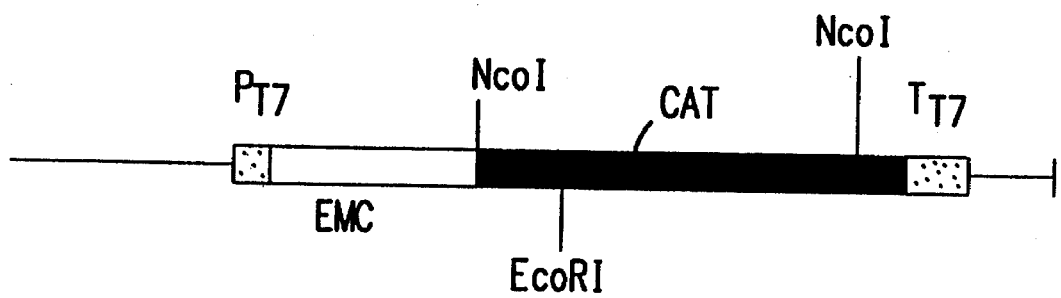

Construction of PT7CAT was carried out in a similar fashion as that of pT7hGH. A 1.7 kbp DNA fragment containing CAT gene was isolated from pBLCAT3, blunt ended with Klenow fragment and dNTPs, and inserted into SmaI site of pTM-I by ligation. The relative position of ATG codon of CAT gene to the T7 promoters was also adjusted to the optimal position by a deletion mutation (FIG. 3B). The adjustments for both hGH and CAT genes did not result in mutations in their amino acid sequences.

Following construction of pT7T7 and pT7hGH, a single plasmid, pT7T7/T7hGH, was constructed from these sequences. As shown in FIG. 4, pT7T7 was linearized at EagI site, the EagI site was subsequently filled by Klenow fragment. A 2.1 kbp ClaI/EagI T7hGH fragment was isolated from pT7hGH, the single stranded cohesive ends were also filled in by Klenow fragment. pT7T7/T7hGH was made by ligating these two sequences together followed by transformation using HMS174 pLysE cells. Large scale preparation of pT7T7/T7hGH, and other plasmid DNA used in these experiments, were made using Qiagen columns (Qiagen).

6.1.4. ADDITION OF POLY(dT) TAILS

The T7 system described herein was designed as a cytoplasmic expression system and therefore no natural poly(A) tails would be added to the hGH and CAT mRNA generated by this system. Poly dT tails of 40 base pairs long were added to the 3' ends of both hGH and CAT genes in order to increase the stability and possibly the translation efficiency of the hGH and CAT mRNA.

6.1.5. TRANSFECTION

Mouse L and human HepG2 cells were grown in growth media in 6-well cell culture dishes to 80% confluence. Plasmid DNA was diluted with water and the T7 buffer (New England Biolabs) to various concentrations in a total volume of 75 µl in sterile polysterene tubes. Alternatively, the T7 buffer may be replaced by saline, PBS or DMEM. Five µl of T7 RNAP (50 U/µl) was added to DNA solution and the mixture was incubated at room temperature for 10 min, followed by addition of 20 µl (1 µg/µl) of lipofectin (Felgner et al., 1987, Proc. Natl. Acad. Sci. USA 84:7413–7417). After gentle mixing, the lipofectin-DNA-enzyme solution was incubated at room temperature for another 5 min. Meanwhile, growth media were removed from L cells, the cells were washed twice with DMEM. One and half ml of DMEM was added to each well, followed by addition of 100 µl of lipofectin-DNA-enzyme solution. After gentle mixing, the dishes were incubated at 37° C. in a cell culture incubator. Following 4 hours of incubation, the media were removed, 2 ml of growth media were added to each well, and the dishes were incubated at 37° C. with 5% $CO_2$. Growth media from the transfected cells were collected every 8 hours for the first 24 hours and then every 24 hours and the cells were replenished with fresh growth media. Cells which were transfected with pT7T7/T7hGH alone, pT7hGH+T7RNAP, or pMThGH were used as expression controls. pMThGH, a conventional expression vector, also served as a reference for comparison of expression profiles. Transfection of pMThGH was performed using a standard lipofection protocol without adding T7 RNAP. In a similar manner, pT7CAT and pT7CAT+T7 RNAP were used as controls for CAT assays, respectively. In DEAE-dextran transfections, DNA-T7 RNAP solution was prepared identically as described for lipofection. After adding DEAE-dextran containing DMEM to DNA-T7 enzyme solution, cells were transfected under the conditions as previously described (Chen et al. (1992) Mol. Endocrinol. 6:598–606).

6.1.6. RADIOIMMUNOASSAY AND CAT ASSAY hGH RIA was performed using a commercially available RIA kit (Hybritech, San Diego). pT7T7, pT7CAT, and T7RNAP were coincubated and transiently transfected into either L or hepG2 cells by the same lipofection protocol as described. Twenty four hours after the transfection, the cells from each well of a 6-well dish were individually harvested in 1 ml PBS, centrifuged and resuspended in 100 µl of 100 mM Tris (pH 7.8). Frozen and thawed three times, the cell debris was removed by centrifugation. The supernatant was incubated at 65° C. for 10 min, followed by centrifugation to remove protein precipitates. The resulting supernatant was assayed for CAT activity as described (Neumann et al., 1987, Biotechniques 5:444–447).

6.1.7. NORTHERN BLOT ANALYSIS

Twenty four or 48 hours after the transfection, transfected cells were lysed by 1 ml of RNAzol (Cinna/Biotecx Laboratories) immediately after PBS wash. Total RNA was isolated as described (Chomczynski and Sacchi, 1987, Anal. Biochem. 162:156–159). Twenty µg of total RNA from each cell sample was subjected to 1% formaldehyde gel electrophoresis. Afterwards, resolved RNA was transferred from the gel to a nylon-based membrane (Gene Screen Plus from NEN), hybridized to a $^{32}$P-labeled, 2.6 kbp T7 fragment and subsequently visualized by autoradiography (Rave et al., 1979, Nucleic Acids Res. 6:3559–3567). After being stripped off the T7 probe, the same membrane was rehybridized to a 0.9 kbp hGH probe. Actin mRNA served as reference controls to standardize sample signal intensities.

6.2. RESULTS

6.2.1. CONSTRUCTION OF PLASMIDS

FIGS. 2, 3A, 3B and 4 schematically demonstrate the construction of the plasmids, pT7T7, pT7hGH, pT7CAT, and PT7T7/T7hGH. The pT7T7 and pT7T7/T7hGH plasmids were grown in the presence of the pLysE plasmid to reduce the toxicity of the T7 enzymes to E. coli. Therefore, these plasmid preparations were always contaminated with some pLysE plasmid ($\leq$10%). Since pT7CAT and pT7hGH were not toxic to their bacterial hosts, their replication did not require pLysE.

Efforts were made to construct T7T7 sequence in order to reduce the cytotoxicity to such levels as to allow sufficient quantities of the plasmids to be prepared from bacterial cells for eukaryotic expression studies. Most of the genetic manipulations were similar to those used in construction of T7 vectors for the expression of cloned genes in bacteria (Studier, 1991, J. Mol. Biol. 219:37–44; Dubendorff et al., 1991, J. Mol. Biol. 219:61–68; Dubendorff et al., 1991, J. Mol. Biol. 219:45–59). However, the goal of making expression systems functioning in eukaryotic cells, not in bacterial cells, permitted more genetic modifications such as the removal of S-D box from the T7 gene, to further minimize its toxicity to E. coli host cells (FIG. 2). These manipulations are advantageous with respect to increasing plasmid yields and reducing the risk of DNA mutations resulted from the selective pressure exerted upon the host cells by the toxic effects of the expressed T7 RNAP.

6.2.2. COMPARISON OF LIPOFECTIN AND DEAE-DEXTRAN TRANSFECTIONS

In order to determine which DNA delivery methods worked more efficiently for the T7 system, both lipofectin or DEAE-dextran transfection methods were compared on the same 6-well cell culture plates. Table I shows the relative transfection efficiencies of lipofection and DEAE-dextran methods on the T7 expression systems. CAT assays, compared to hGH assays, resulted in smaller standard deviations largely due to the higher sensitivity of the assays while hGH assays could not as accurately detect low levels of hGH expression from DEAE-dextran transfected cells. As indicated by Table I, lipofection was approximately 8–10 times more efficient than DEAE-dextran method for the T7 expression system.

The key for the success of the expression of the T7 systems in eukaryotic cells is to keep the T7 RNAP tightly bound in undegraded forms to the DNA during the process of transfection. It is possible that liposomes better protected the DNA-T7 enzyme complex and/or better facilitated the complex to reach the cytoplasm of the cells.

TABLE I

Comparison of relative transfection efficiencies.

| Transfection Method | Relative hGH activity | Relative CAT Activity |
|---|---|---|
| Lipofection | 100 | 100 |
| DEAE-dextran | 11.5 ± 4.6 | 14.2 ± 3.9 |

6.2.3. TRANSIENT EXPRESSION OF THE FUNCTIONAL/REPORTER GENES

6.2.3.1. hGH EXPRESSION

The expression of pT7T7+pT7hGH (dual plasmid) or pT7T7/T7hGH (single plasmid) in L cells as compared to pT7hGH and pMThGH is shown in FIG. 5. Cell culture supernatants from transiently transfected L cells were collected and assayed for hGH every 8 hours for the first 24 hours and then every 24 hours for 5 days. By day 7, the cells were severely overgrown in the well and started to die.

Detectable levels of hGH were found as early as 8 hours after transfection in cell culture fluids collected from cells transfected either by pT7T7+pt7hGH+T7 RNAP or pT7T7/T7hGH+T7 RNAP. The hGH in the culture medium of transfected L cells was biologically active in stimulating rat Nb2 cells. However, expression of pMThGH (which served as positive control as well as a reference for expression profiles in this study) could not be detected until 24 hours after the transfection. The expression of hGH by pMTbGH was not higher than that of the T7 system until 72 hours or later. For cell samples transfected by pT7hGH plus T7 RNAP (negative control I), only the culture medium collected 8 hours after the transfection demonstrated low levels of hGH (FIG. 5). The expression disappeared after longer incubation periods. This indicates that it was the post-transfection expression of the T7 gene that maintained expression of the hGH gene. No hGH could be detected at any time in the culture fluids collected from the cells transfected by pT7T7/T7hGH alone without prebound T7 RNAP. The expression of the T7 system reached its peak (~3 ng/ml) approximately 24 to 48 hours after the transfection whereas expression of pMThGH reached its peak (~7 ng/ml) at about 96 to 120 hours. Therefore, the kinetics of the hGH expression by the T7 system seemed to be quite different from that of a traditional expression vector.

The onset of expression of hGH using the T7 system was more rapid than that of a conventional mammalian promoter-containing plasmid pMThGH. This result was consistent with studies using a T7CAT vector coupled with recombinant vaccinia viruses, which showed that 48 hours after the transfection the cells transfected by the T7 system produced several hundred-fold higher CAT activities than those expressed either RSVCAT or SV40CAT (Fuerst et al., 1986, Proc. Natl. Acad. Sci. USA 83:8122–8126). The rapid expression and different kinetics exhibited by the T7 system indicate that an expression mechanism, which differs from the one used by pMTbGH, was employed by the T7 system. It is likely that the plasmid-bound T7 RNAP initiated transcription immediately after the plasmids were taken into the cytoplasm of the cells, followed by rapid protein synthesis and secretion which resulted in the shift the expression curves to the left. In contrast, pMTbGH had to reach the nuclei of the transfected cells for the hGH expression which may explain the long delay of the hGH expression by pMThGH. This result is consistent with those of other studies which showed that reporter gene was actively transcribed by T7 RNAP in the cytoplasm of cells (Fuerst et al., 1986, Proc. Natl. Acad. Sci. USA 83:8122–8126; Elroy-Stein et al., 1990, Proc. Natl. Acad. Sci. USA 87:6743–6747). It is also consistent with the cytoplasmic expression nature of the T7 parental plasmid pTM-I (Moss et al., 1990, Nature 348:91–92). Because of the rapid and efficient expression in the early hours post transfection compared to other conventional plasmid systems, this T7 expression system may prove to be useful to express cDNA in those circumstances in which rapid assays are desirable.

6.2.3.2. CAT EXPRESSION

FIG. 6 demonstrates the results of CAT assays. Cells were lysed and assayed 48 hours after the transfection. CAT activities in pT7T7+pT7CAT+T7 RNAP transfected cells were over 50 times more than that of the PT7CAT+T7 RNAP transfected samples (negative control type I) and were more than 100 times that of pT7CAT transfected samples (negative control type II). On the basis of absolute quantity, it turned out that the intracellular CAT activity corresponded to approximately 2–3 ng CAT protein/well (or per $10^6$ cells), in the same range of magnitude as extracellular hGH levels expressed by either PT7T7/T7hGH+T7 RNAP or pT7T7+pT7hGH+T7 RNAP.

6.2.4. NORTHERN ANALYSIS OF T7 mRNA

In order to prove that the sustained expression of the functional/reporter genes in the T7 system was indeed due to the sustained expression of the T7 genes in the same system, total RNA from the transfected cells was isolated and analyzed by Northern blots as shown in FIG. 7. Both T7 RNAP and hGH mRNA were found in the cells transfected by pT7T7/T7hGH+T7 RNAP, but not in the cells transfected either by pT7T7/T7hGH alone or by pT7hGH+T7 RNAP (FIGS. 7-I and II). The position of the major bands on the blots corresponded to the anticipated sizes of the T7 RNAP and hGH mRNA. Also, the levels of T7 and hGH mRNA were found to correlate with each other, i.e., the higher the T7 mRNA level (24 hr), the higher the hGH mRNA level, and vice versa (48 hr samples).

6.2.5. EXPRESSION OF hGH AND CAT IN BOTH L AND HepG2 CELLS

Expression of hGH and CAT by mouse L and human HepG2 cells transfected by pT7T7+pT7hGH or pT7T7+pT7CAT is summarized in Table II. Because the two cell types grew in very different modes (L cells grew in a single uniform layer whereas HepG2 cells grew in clusters), hGH and CAT levels per well were found to be quite different for the two cell types. However, when the expression levels were adjusted on the basis of each mg of cell proteins, it was found that L cells and HepG2 cells expressed both genes, particularly the CAT gene, with comparable efficiencies (Table II).

TABLE II

Relative expression efficiencies by different cell lines.

| Cell lines | Relative hGH activity | Relative CAT Activity |
|---|---|---|
| Mouse L cells | 100 | 100 |
| Human HepG2 cells | 268 ± 51 | 177 ± 25 |

7. EXAMPLE: T7 RNA POLYMERASE PREBOUND TO DNA DIRECTS GENE EXPRESSION IN IN VIVO TISSUES

7.1. MATERIALS AND METHODS

7.1.1. CONSTRUCTION OF PLASMID

In order to construct a pT7T7/T7Luc plasmid, a pT7Luc plasmid was first constructed by insertion of a luciferase cDNA (de Wet et al., 1987, Mol. Cell. Biol. 7:725–737) into pTM-I, followed by cleavage of ClaI/EagI T7-luciferase fragment from pT7Luc, and insertion of the blunt-ended T7-luciferase fragment into blunt-ended EagI site of pT7T7.

7.1.2. IN VIVO ADMINISTRATION

Varying concentrations of plasmids pT7T7/T7 Luc and pT7T7/T7hGH were complexed with T7 RNAP in a solution with or without lipofectin and injected directly into mouse tail, liver, leg muscles, cerebrospinal fluids or intravenously. Injection was performed by injecting 70–100 µl of DNA-T7 RNAP in saline, PBS or DMEM into animal tissues using 25-gauged needles. After a certain time period, gene expression was assessed by sacrificing the animals and a portion of specific tissues was removed. In the case of luciferase expression, the tissue was homogenized in 200–400 µl of luciferase lysis buffer, and 10 µl of the tissue extract was assayed for luciferase activities using a commercially available kit from Promega. In the case of growth hormone expression, cerebrospinal fluids, brain tissues and sera were assayed for hGH activity by commercially available radioimmunoassay kits.

7.2. RESULTS

In order to facilitate the detection of gene expression in vivo, the luciferase gene was chosen and inserted into the expression system of the invention as pT7T7/T7Luc. When the plasmid DNA was complexed with T7kNAP in vitro and injected with lipofectin into the connective tissues of the tail of mice subcutaneously, a high level of luciferase activity was detected in homogenized tail tissues 24 hours after injection (FIG. 8). This response was dose-dependent, and luciferase gene expression was detectable for at least one week. Control plasmids did not produce detectable activities. When the same material was injected into the tail vein of mice intravenously, and the tail vein was dissected from the rest of the tail tissues about 24 hours later, the luciferase activity detected in these cells was over a million times more than that in the tail tissues, as compared by tissue weight. This indicates that intravenous injection of DNA-RNAP complex may be taken up immediately by endothelial cells leading to rapid expression of the gene product, especially near the site of injection.

Similarly, when pT7T7/T7Luc with prebound T7 RNAP was injected into the mouse leg muscles intramuscularly, into mouse livers intrahepatically or into the cerebrospinal fluids of 20 day-old mice intracranially, significant luciferase activity was observed in muscle tissues (FIG. 9), in mouse livers (FIG. 10) and in brain tissues (FIG. 11).

The pT7T7/T7hGH plasmid encoding secreted human growth hormone was also tested in vivo. The DNA was complexed with T7 RNAP and liposome, and injected into the cerebrospinal fluids of 20 day-old mice. Growth hormone activity was detected in both cerebrospinal fluids and brain tissues from the injected animals 20 hours after injection (FIG. 12).

In addition, when 100 μg of pT7T7/T7hGH plasmid complexed with T7 RNAP in the absence of lipofectin was injected into the connective tissues of the tail of mice subcutaneously, 200–300 pg/ml of human growth hormone was detected in the peripheral blood the following day.

The present invention is not to be limited in scope by the exemplified embodiments which are intended as illustrations of single aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

not require mammalian host cell factors; and an exogenous RNA polymerase which transcribes said coding sequence from said cognate promoter, and which polymerase is co-delivered with said DNA molecule into mammalian cells.

4. The expression system of claim 3 in which the RNA polymerase is derived from a bacteriophage selected from the group consisting of T7, T3, SP6 and K11.

5. The expression system of claim 4 in which the gene of interest encodes a protein.

6. The expression system of claim 5 in which the gene of interest encodes human growth hormone.

7. The expression system of claim 5 in which the gene of interest encodes chloramphenicol acetyltransferase.

8. The expression system of claim 5 in which the gene of interest encodes luciferase.

---

---

What is claimed is:

1. A gene expression system in mammalian cells comprising a recombinant DNA molecule which comprises a coding sequence for an RNA polymerase having transcriptional activity that does not require mammalian host cell factors or a functional derivative thereof, operably linked to its cognate promoter; and an exogenous RNA polymerase which transcribes said coding sequence from said cognate promoter, and which polymerase is co-delivered with said DNA molecule into mammalian cells.

2. The expression system of claim 1 is which the RNA polymerase coding sequence is derived from a bacteriophage selected from the group consisting of T7, T3, SP6 and K11.

3. A gene expression system in mammalian cells comprising a recombinant DNA molecule which comprises a coding sequence for a gene of interest or a functional derivative thereof, operably linked to a cognate promoter for an RNA polymerase having transcriptional activity that does 9. The expression system of claim 4 in which the gene of interest encodes an anti-sense RNA.

10. The expression system of claim 4 in which the gene of interest encodes a ribozyme molecule.

11. A gene expression system in mammalian cells comprising a recombinant DNA molecule which comprises a coding sequence for an RNA polymerase having transcriptional activity that does not require mammalian host cell factors or a functional derivative thereof, operably linked to its cognate promoter, and a coding sequence for a gene of interest or a functional derivative thereof, operably linked to a second copy of the cognate promoter; and an exogenous RNA polymerase which transcribes said coding sequences from said cognate promoter, and which polymerase is co-delivered with said DNA molecule into mammalian cells.

12. The expression system of claim 11 in which the RNA polymerase coding sequence is derived from a bacteriophage selected from the group consisting of T7, T3, SP6 and K11.

13. The expression system of claim 12 in which the gene of interest encodes a protein.

14. The expression system of claim 13 in which the gene of interest encodes human growth hormone.

15. The expression system of claim 13 in which the gene of interest encodes chloramphenicol acetyltransferase.

16. The expression system of claim 13 in which the gene of interest encodes luciferase.

17. The expression system of claim 12 in which the gene of interest encodes an anti-sense RNA.

18. The expression system of claim 12 in which the gene of interest encodes a ribozyme molecule.

19. A method for expressing an exogenous gene in mammalian cells comprising:
(a) co-delivering into mammalian host cells:
  (i) a recombinant DNA molecule which comprises a coding sequence for an RNA polymerase having transcriptional activity that does not require mammalian host cell factors or a functional derivative thereof, operably linked to its cognate promoter;
  (ii) a second recombinant DNA molecule which comprises a coding sequence for a gene of interest or a functional derivative thereof, operably linked to a second copy of the cognate promoter of (i); and
  (iii) an exogenous RNA polymerase which transcribes said coding sequences from said cognate promoters; and
(b) inducing expression of the gene of interest in the cells.

20. The method of claim 19 in which the RNA polymerase coding sequence is derived from a bacteriophage selected from the group consisting of T7, T3, SP6 and K11.

21. The method of claim 20 in which the gene of interest encodes a protein.

22. The method of claim 21 in which the gene of interest encodes human growth hormone.

23. The method of claim 21 in which the gene of interest encodes human chloramphenicol acetyltransferase.

24. The method of claim 21 in which the gene of interest encodes luciferase.

25. The method of claim 20 in which the gene of interest encodes an anti-sense RNA.

26. The method of claim 20 in which the gene of interest encodes a ribozyme molecule.

27. A method for expressing an exogenous gene in mammalian cells comprising:
(a) co-delivering into mammalian host cells:
  (i) a recombinant DNA molecule which comprises a coding sequence for an RNA polymerase having transcriptional activity that does not require mammalian host cell factors or a functional derivative thereof, operably linked to its cognate promoter, and a coding sequence for a gene of interest or a functional derivative thereof, operably linked to a second copy of the cognate promoter; and
  (ii) an exogenous RNA polymerase which transcribes said coding sequences from said cognate promoters: and
(b) inducing expression of the gene of interest in the cells.

28. The method of claim 27 in which the RNA polymerase coding sequence is derived from bacteriophage T7.

29. The method of claim 28 in which the gene of interest encodes a protein.

30. The method of claim 29 in which the gene of interest encodes human growth hormone.

31. The method of claim 29 in which the gene of interest encodes chloramphenicol acetyltransferase.

32. The method of claim 29 in which the gene of interest encodes luciferase.

33. The method of claim 28 in which the gene of interest encodes an anti-sense RNA.

34. The method of claim 28 in which the gene of interest encodes a ribozyme molecule.

35. The expression system of claim 1, 3 or 11 in which the DNA molecular further comprises a capping independent sequence that allows the translation of uncapped RNA in mammalian cells.

36. The expression system of claim 35 in which the capping independent sequence is derived from encephalomyocarditis virus.

37. The method of claim 19 or 27 in which the DNA molecular further comprises a capping independent sequence that allows the translation of uncapped RNA in mammalian cells.

38. The method of claim 37 in which the capping independent sequence is derived from encephalomyocarditis virus.

* * * * *